(12) United States Patent
Han et al.

(10) Patent No.: US 6,562,374 B1
(45) Date of Patent: May 13, 2003

(54) BIODEGRADABLE POROUS POLYMER SCAFFOLDS FOR TISSUE ENGINEERING PREPARED FROM AN EFFERVESCENT MIXTURE AND ITS PREPARATION

(75) Inventors: Dong Keun Han, Seoul (KR); Kwang-Duk Ahn, Seoul (KR); Jong-Man Kim, Seoul (KR); Young Min Ju, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/699,213

(22) Filed: Oct. 27, 2000

(30) Foreign Application Priority Data

Jun. 23, 2000 (KR) ......................................... 2000-34935

(51) Int. Cl.[7] .............................. C08J 9/00; C08J 9/08; C08J 9/20; C08J 9/28; C08J 9/14
(52) U.S. Cl. ....................... 424/484; 424/426; 424/444; 435/399; 514/802; 514/945; 514/955; 521/98; 521/84.1; 521/113; 521/51
(58) Field of Search ................................. 424/484, 426, 424/422, 444; 435/399; 514/802, 945, 955; 521/98, 84.1, 113, 51

(56) References Cited

U.S. PATENT DOCUMENTS 6,281,256 B1 * 8/2001 Harris et al. ................ 521/123

FOREIGN PATENT DOCUMENTS

KR WO 00/55300 A1 * 9/2000

* cited by examiner

*Primary Examiner*—Frederick Krass
*Assistant Examiner*—Clinton Ostrup
(74) *Attorney, Agent, or Firm*—Darby & Darby

(57) ABSTRACT

The present invention provides a method for preparing biodegradable porous polymer scaffolds for tissue engineering, comprising:
  a) fabricating a polymer sample from a polymer solution containing at least one biodegradable polymer and an effervescent mixture;
  b) effervescing the polymer sample in the presence of an effervescent medium such as an aqueous alcohol solution; and
  c) drying.

The method for preparing biodegradable polymer scaffolds of the present invention has the advantages that the process is simple, that pore size can be easily controlled, that the problem caused by the secretion and existence of the toxic substance can be avoid by using a material harmless to human body, and that high efficiency can be achieved. In addition, biodegradable porous polymer scaffolds prepared by above method have the advantages that high porosity can be achieved and an open cell structure in which pores are interconnected is obtained.

16 Claims, 1 Drawing Sheet

BIODEGRADABLE POROUS POLYMER SCAFFOLDS FOR TISSUE ENGINEERING PREPARED FROM AN EFFERVESCENT MIXTURE AND ITS PREPARATION

This application claims priority under 35 U.S.C. §119 from Republic of Korea Patent Application Serial No. 34935/2000, filed Jun. 23, 2000, the disclosure of which is incorporated herein by reference in its entirety.

BACKGROUND OF THE INVENTION

1. Field of the Invention

The present invention relates to a method for preparing biodegradable porous polymer scaffolds for tissue engineering, comprising:

a) fabricating sample from a polymer solution containing biodegradable polymer and effervescent mixture;

b) effervescing (foaming) the obtained polymer sample in the presence of an effervescent medium such as an aqueous alcohol solution; and c) drying.

The present invention also relates to a biodegradable porous polymer scaffold for tissue engineering prepared by adopting the above method, which has a proper pore size, a high porosity and an open cell structure in which pores are interconnected.

2. Description of the Background Art

Tissue engineering which is one of the new fields opened with the development of the science and which is an applied study that utilize the basic concept and technique of life science and engineering gives a clue to understand co-relationship between a structure and a function of body tissue and make a substitute of the body tissue for transplantation, thereby to maintain, improve or restore the function of human body.

One of the typical tissue engineering techniques comprises taking out a required tissue from a patient body, followed by isolating cell from the tissue, proliferating the isolated cell, seeding the cell in the biodegradable porous polymer scaffolds, culturing the cell in vitro for a predetermined period, and then, transplanting the obtained hybrid-type cell/polymer structure into the human body. After transplantation is achieved, by virtue of diffusion of body fluids, oxygen and nutrients are provided to transplanted cells in biodegradable porous polymer until a blood vessel is newly formed. When a blood vessel is formed to which blood is supplied, the cells are cultivated and divided to form a new tissue and an organ. During new tissue and the organ form, the polymer scaffolds are degraded and disappear.

Accordingly, in the field of tissue engineering, it is important to prepare a biodegradable porous polymer scaffold that is similar to the body tissue.

In order to be used as a raw material of the polymer scaffolds, the material should serve as a matrix or a frame properly so that tissue cells can adhere to the surface of a material to form a tissue in a three-dimensional structure. It should also serve as a middle barrier positioned between a transplanted cell and a host cell. That is, it should be non-toxic and biocompatible such that neither blood coagulation nor inflammatory reaction occurs after transplantation.

In addition, it should be biodegradable such that as the transplanted cell functions properly as a tissue, it is completely degraded in vivo within a desired time.

Biodegradable polymers widely used as raw materials for the scaffold include polyglycolic acid (PGA), polylactic acid (PLA), lactic acid-glycolic acid copolymer (PLGA), poly-ε-caprolactone (PCL), polyamino acid, polyanhydride, polyorthoester, and copolymers thereof. However, to date, only PGA, PLA, and PLGA are approved as biodegradable polymers acceptable for use in human body by the U.S. FDA, and are being used as raw materials for biodegradable porous polymer scaffolds for regeneration within human body.

Meanwhile, recently, researchers have made various attempts to prepare polymer having a porous structure, for example, solvent-casting and particulate-leaching technique (A. G. Mikos, etc. Polymer, 35, 1068, 1994), wherein single crystal NaCl is mixed, dried and dissolved in water; gas forming technique (L. D. Harris, etc., Journal of Biomedical Materials Research, 42, 396, 1998), wherein polymer is inflated by using $CO_2$ gas; fiber extrusion and fabric forming process (K. T. Paige, etc. Tissue Engineering, 1, 97, 1995), wherein polymer fiber is made to a nonwoven fabric to make a polymer mesh; thermally induced phase separation technique (C. Schugens, etc., Journal of Biomedical Materials Research, 30, 449, 1996), wherein solvent contained in the polymer solution is immersed in a nonsolvent to make porosity; and emulsion freeze-drying method (K. Whang, etc. Polymer, 36, 837, 1995), wherein polymer solution are mixed with water to make emulsion, which is then frozen with liquid nitrogen and freeze-dried.

However, with the conventional methods, it is not easy to control the size of the pores, porosity is comparatively low, and open structure is not formed well between pores. In addition, these methods have disadvantages in that the closed pore phenomenon occurs on the surface of the scaffolds, process is comparatively complicated, gas or toxic substance is secreted during the preparation of scaffolds, and salt remains in the scaffolds.

SUMMARY OF THE INVENTION

Therefore, an object of the present invention is to provide a new method that can substitute the solvent-casting and particulate-leaching technique and the gas forming technique that have been generally adopted to prepare a biodegradable porous polymer scaffold.

Another object of the present invention is to provide a novel method for preparing a biodegradable porous polymer scaffold for tissue engineering that can solve problems of the close pore phenomenon on the surface of the scaffolds, the complicate process, the secretion of toxic substance and the salt-remaining phenomenon.

Still another object of the present invention is to provide a novel method for preparing a biodegradable porous polymer scaffold in which the pore size is easily controlled.

Yet another object of the present invention is to provide biodegradable polymer scaffolds for tissue engineering that has high porosity and an open cell structure in which pores are interconnected with each other.

These and other objects described in the specification can be achieved by providing a method for preparing biodegradable porous polymer scaffolds, which comprises making a polymer sample from a polymer solution containing biodegradable polymer and effervescent mixture, effervescing (foaming) the polymer sample in the presence of an effervescent medium such as an aqueous alcohol solution, and drying, and biodegradable porous polymer scaffolds prepared by the method.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1A:
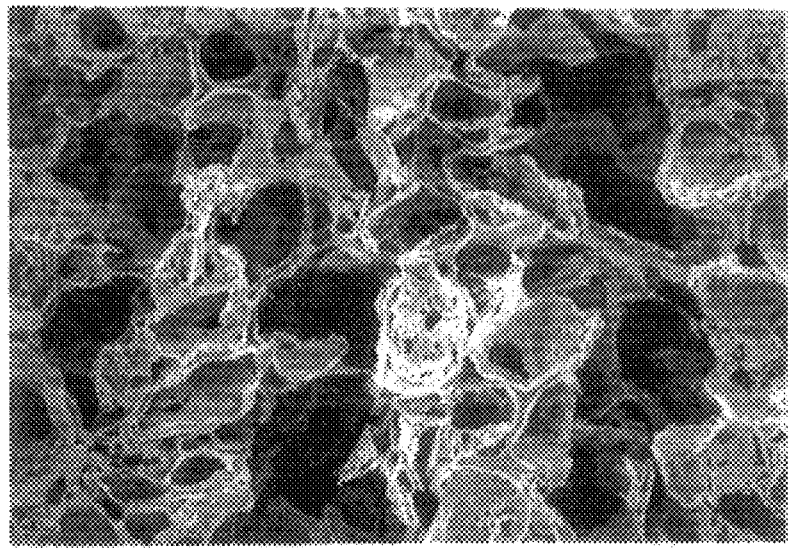
FIG. 1A is a scanning electron microscope (SEM) photograph showing an outer surface of scaffolds made from polylactic acid.

The inventors of the present invention conducted a research to solve the above problems of the conventional preparation method of the polymer scaffolds and have achieved a novel method for preparing a biodegradable polymer scaffold for tissue engineering from an effervescent mixture and a biodegradable polymer harmless to human body. The method utilizes a method for preparing an effervescent tablet used for the preparation of a gastrointestinal remedy or a dental effervescent drug preparation. In other words the method utilizes a principle that pores are formed by the effervescence of CO2, which are resulted from the addition of polymer solution containing both organic acids and carbonate to water.

The method for preparing biodegradable porous polymer scaffolds comprises:

a) fabricating a polymer sample from a polymer solution containing at least one biodegradable polymer and an effervescent mixture;

b) effervescing the polymer sample in contact with an effervescent medium such as an aqueous alcohol solution; and c) drying.

More specifically, the method comprises:

a) applying a polymer solution containing at least one biodegradable polymer and an effervescent mixture to a frame made of a polymer material, evaporating the solvent, thereby fabricating a disk-type polymer sample;

b) effervescing the disk-type polymer sample in contact with the effervescent medium such as a mixed solution of water and alcohol; and c) washing the sample passed through the effervescing process with water and drying.

a) Fabrication of a polymer sample

First, a biodegradable polymer is dissolved in an appropriate solvent in the same manner as in the solvent-casting and particulate-leaching technique, and an effervescent mixture for generating pores is added therein, and then the obtained solution is uniformly mixed. This mixed solution is applied to a frame having a desired form, for example, made of a silicon material. As the solvent is evaporated to a certain degree, a disk-type sample is fabricated.

The biodegradable polymer used in the present invention is a non-toxic polymer and it is biodegradable in the human body. For example, polyglycolic acid (PGA), polylactic acid (PLA), lactic acid-glycolic acid copolymer (PLGA), poly-ε-caprolactone (PCL), polyamino acid, polyanhydride, polyorthoester, and copolymers thereof can be used as a biodegradable polymer, but not limited thereto.

Among them, it is preferred to use polyglycolic acid (PGA), polylactic acid (PLA), copolymers of polylactic acid-glycolic acid (PLGA) or mixtures thereof that have been approved as biodegradable polymers acceptable for use in human body by the U.S. FDA. Molecular weight of the biodegradable polymer is preferably 5,000–2,000,000, and more preferably 10,000–700,000, but not limited thereto.

The concentration of the polymer solution is preferably 5–15 wt % and as a solvent, chloroform, dichloromethane, acetone, dioxane, tetrahydrofuran and mixtures thereof may be used.

The effervescent mixture used in the present invention for forming pores comprises carbonate and organic acid. The effervescent mixture comprising carbonate and organic acid is a harmless substance to human body that can be used in a common medicine and is a solid which is easily dissolved in water and which has a certain size.

Carbonate is preferably selected from the group consisting of sodium bicarbonate, sodium carbonate, ammonium bicarbonate, ammonium carbonate, potassium bicarbonate, potassium carbonate, calcium carbonate, and mixtures thereof which generate carbon dioxide. And organic acid is preferably selected from the group consisting of citric acid, tartaric acid, succinic acid, maleic acid, fumaric acid, malonic acid, malic acid, gluconic acid, mucic acid, a certain amino acid and mixtures thereof.

The particle size of the effervescent mixture depends on the use, for which, typically, 10–500 μm is suitable. The weight ratio of the effervescent mixture to the polymer is preferably 5/1–20/1. In the effervescent mixture, molar ratio of organic acid to carbonate is preferably in the range from 1:1 to 1:3. In case two or more organic acids are used, the ratio of the organic acids depends on the molar ratio of carboxyl groups.

b) Effervescence of the polymer sample obtained in step a)

The disk-type polymer sample as obtained in step a) is subjected to a process of effervescence. Effervescence is preferably performed in contact with a mixed solution medium of water and alcohol to remove the residual organic solvent and lead to immersion of the scaffolds.

Alcohol for use in the mixed aqueous solution includes ethanol, methanol or isopropyl alcohol, and its content is suitably 1–95 volume %.

In addition, when $CO_2$ is generated by adding the effervescent mixture to a effervescing medium, that is, when $CO_2$ is effervescing, physical method including ultrasonic, microwave or agitation can be additionally performed in order to effectively perform an effervescence, and to prevent lifting of a polymer scaffold due to the attachment of generated gases to the scaffolds, c) Drying After passing through the effervescing step, the polymer sample is washed with ultra-pure water and dried to make a biodegradable polymer scaffold. In this respect, in order to minimize shrinkage phenomenon which may be caused by the rapid evaporation of the excess water and residual organic solvent contained in the porous scaffold, it is preferred that the polymer sample is freeze-dried, or vacuum-dried at room temperature or below the glass transition temperature of the biodegradable polymers used.

The biodegradable polymer scaffold fabricated through the several processes is analyzed using the scanning electron microscope (SEM), which are depicted in FIGS. 1A (picture of the outer surface) and 1B (picture of the inner section).

Figure 1B:
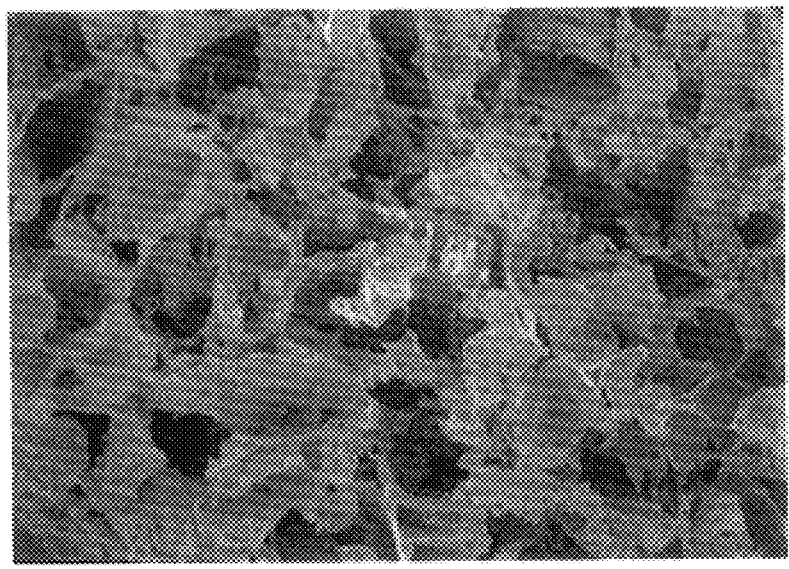
FIG. 1B is a scanning electron microscope (SEM) photograph showing an inner section of scaffolds made from polylactic acid.

As shown in FIGS. 1A and 1B, through its inner section and outer section, the biodegradable polymer scaffold of the present invention had a uniform size and distribution of pores, and the pore size was almost the same as the particle size of the effervescent mixture used for forming a pores, and especially, no close pore on the outer surface of the scaffolds was observed and it had a open cell structure in which pores were interconnected. Results obtained by a mercury porosimetry analyzer calculating a porosity showed that the overall porosity was roughly in the range of 93~98%.

Hereinafter, the present invention will be clearly understood by the following Examples, but the scope of the invention is not limited thereto.

EXAMPLES

Example 1

Polylactic-glycolic acid (PGLA) containing lactic acid and glycolic acid in the weight ratio of 50:50 and having a molecular weight of about 110,000 was added into chloroform such that 13 wt % chloroform solution was obtained, and then, the solution was evenly agitated using a magnetic bar in order to obtain a homogeneously dissolved solution.

An effervescent mixture containing sodium bicarbonate and citric acid having about 200~300 µm of size, wherein molar ratio of sodium carbonate to citric acid is 3:1, was added to the PLGA solution in the ratio of the mixture/PLGA was 20/1 by weight, and homogeneously mixed.

The mixed solution was applied to a frame made of a silicon material having a desired form and left for about 30 minutes to evaporate the solvent to a certain degree such that a disk-type sample was fabricated.

While ultrasonification was applied, the disk-type sample was added to a mixed solution of water and ethanol (the volumetric ratio is 50:50) and effervescence was taken place for about 20 hours. And then, the sample was taken out and applied to freeze-drying for 20 hours.

Thusly fabricated cubic porous polymer scaffold showed the almost same porosity form and distribution through the outer and the inner section, and the pore size was similar to that (200~300 µm) of the effervescent mixture as used.

In addition, no close pore was observed in the outer surface of the scaffold and the scaffolds having the open cell structure in which pores are interconnected was obtained. The overall porosity of the scaffold was about 98%.

Example 2

An effervescent mixture containing sodium carbonate and citric acid (the size: 200~300 um), wherein the molar ratio of sodium carbonate to citric acid is 1:1, was added to poly-L-lactic acid (PLLA) solution in which 5 wt % PLLA having a molecular weight of about 2,000,000 was dissolved in a dichloromethane, of which the weight ratio of the effervescent mixture to the PLGA was 5/1, and evenly mixed.

The mixed solution was applied to a frame made of a silicon material having a desired form and left for about 30 minutes to evaporate the solvent to a certain degreee such that a disk-type sample was fabricated.

While ultrasonication was applied, the disk-type sample was added to a mixed solution of water and ethanol (the volumetric ratio is 50:50) and effervescence was taken place for about 20 hours. And then, the sample was taken out and applied to freeze-drying for 20 hours.

Thusly fabricated cubic porous polymer scaffolds, likewise in the Example 1, showed the almost same porosity form and distribution through the outer and the inner section, and the pore size was similar to that (200~300 um) of the effervescent mixture as used.

In addition, no close pore was observed in the outer surface of thge scaffold and the scaffolds having the open cell structure in which pores are interconnected was obtained. The overall porosity of the scaffold was about 96%.

Example 3

In the same manner as Example 1, the procedure was performed except that polylactic-glycolic acid (PLGA) solution containing lactic acid and glycolic acid in the weight ratio of 75:25 and having a molecular weight of about 20,000 was used instead of polylactic-glycolic acid (PGLA) containing lactic acid and glycolic acid in the weight ratio of 50:50 and having a molecular weight of about 110,000, that acetone was used instead of chloroform, that an effervescent mixture containing ammonium bicarbonate and tartaric acid having porous size of 300~400 µm was used instead of an effervescent mixture containing sodium bicarbonate and citric acid having about 200~300 µm of size, and that vacuum drying at room temperature were done instead of freeze-drying.

The obtained cubic porous polymer scaffolds showed the almost same porosity form and distribution through the outer and the inner section, and the pore size was similar to that (200~300 µm) of the effervescent mixture as used.

In addition, no close pore was observed in the outer surface of the scaffold and the scaffolds having the open cell structure in which pores are interconnected was obtained. The overall porosity of the scaffold was about 95%.

Example 4

In the same manner as Example 1, the procedure was performed except that polylactic-glycolic acid (PLGA) solution containing lactic acid and glycolic acid in the weight ratio of 85:15 and having a molecular weight of about 220,000 was used instead of polylactic-glycolic acid (PGLA) containing lactic acid and glycolic acid in the weight ratio of 50:50 and having a molecular weight of about 110,000, and that an effervescent mixture containing sodium bicarbonate and sodium carbonate (1:1 wt %) and organic acids (citric acid:tartaric acid=1:1 wt %) having porous size of 400~500 µm was used instead of an effervescent mixture containing sodium bicarbonate and citric acid having about 200~300 µm of size.

The obtained cubic porous polymer scaffolds showed the almost same porosity form and distribution through the outer and the inner section, and the pore size was similar to that (200~300 µm) of the effervescent mixture as used.

In addition, no close pore was observed in the outer surface of the scaffold and the scaffolds having the open cell structure in which pores are interconnected was obtained. The overall porosity of the scaffold was about 93%.

Example 5

In the same manner as Example 1, the procedure was performed except that poly-D,L-lactic acid (PDLLA) dioxane solution containing 8 wt % of PDLLA having a molecular weight of about 5,000 was used instead of polylactic-glycolic acid (PGLA) chloroform solution containing lactic acid and glycolic acid in the weight ratio of 50:50 and having a molecular weight of about 110,000, that an effervescent mixture containing ammonium carbonate and succinic acid having porous size of 100~200 µm was used instead of an effervescent mixture containing sodium bicarbonate and citric acid having about 200~300 µm of size, and that an effervescent medium containing water and ethanol in the volumetric ratio of 95:5 was used instead of an effervescent medium containing in the volumetric ratio of 50:50.

The obtained porous polymer scaffold showed the same result as that of the Example 1.

Example 6

In the same manner as Example 1, the procedure was performed except that poly-ε-caprolactone (PCL) tetrahydrofuran solution containing 13 wt % of PCL having a molecular weight of about 100,000 was used instead of polylactic-glycolic acid (PGLA) chloroform solution containing lactic acid and glycolic acid in the weight ratio of 50:50 and having a molecular weight of about 110,000, that an effervescent mixture containing potassium bicarbonate and maleic acid was used instead of an effervescent mixture containing sodium bicarbonate and citric acid, and that an effervescent medium containing water and ethanol in the volumetric ratio of 5:95 was used instead of an effervescent medium containing in the volumetric ratio of 50:50.

The obtained porous polymer scaffold showed the same result as that of the Example 1.

Example 7

In the same manner as Example 1, the procedure was performed except that 15 wt % copolymer chloroform solution containing glycolic acid and ε-caprolactone in the weight ratio of 50:50 and having a molecular weight of 220,000 was used instead of 13 wt % polylactic-glycolic acid (PGLA) chloroform solution containing lactic acid and glycolic acid in the weight ratio of 50:50 and having a molecular weight of about 110,000, and that an effervescent mixture containing potassium carbonate and mucic acid was used instead of an effervescent mixture containing sodium bicarbonate and citric acid.

The obtained porous polymer scaffold showed the same result as that of the Example 1.

Example 8

In the same manner as Example 1, the procedure was performed except that 11 wt % polyorthoester chloroform solution having a molecular weight of about 200,000 was used instead of 13 wt % polylactic-glycolic acid (PGLA) chloroform solution containing lactic acid and glycolic acid in the weight ratio of 50:50 and having a molecular weight of about 110,000, and that an effervescent mixture containing calcium carbonate and asparatic acid was used instead of an effervescent mixture containing sodium bicarbonate and citric acid.

The obtained porous polymer scaffold showed the same result as that of the Example 1.

Example 9

In the same manner as Example 1, the procedure was performed except that polyanhydride having a molecular weight of about 100,000 was used instead of 13 wt % polylactic-glycolic acid (PGLA) having lactic acid and glycolic acid in the weight ratio of 50:50 and having a molecular weight of about 110,000, and that an effervescent mixture containing sodium bicarbonate and glutamic acid was used instead of an effervescent mixture containing sodium bicarbonate and citric acid.

The obtained porous polymer scaffold showed the same result as that of the Example 1.

As so far described, unlike the conventional methods, the method for preparing biodegradable polymer scaffolds of the present invention has the advantages that the process is a simple, that pore size can be easily controlled, that the problem caused by the secretion and existence of the toxic substance can be avoid by using a material harmless to human body, and that high efficiency can be achieved.

In addition, the biodegradable polymer scaffolds fabricated by the method of the present invention has high porosity and an open cell structure in which pores are interconnected, so that almost all damaged tissues and organs of body can be regenerated by tissue engineering.

Accordingly, the method according to the present invention is expected to favorably replace the generally adopted salt leaching technique and the gas foaming technique.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalence of such meets and bounds are therefore intended to be embraced by the appended claims.

What is claimed is:

1. A method for preparing a biodegradable porous polymer scaffold comprising:
    a) fabricating a polymer sample from a polymer solution containing at least one biodegradable polymer and an effervescent mixture comprising a carbonate and an organic acid;
    b) effervescing the polymer sample in contact with an effervescent medium comprising an aqueous alcohol solution; and
    c) drying.

2. The method according to claim 1, wherein the biodegradable porous polymer scaffold has a porosity of 93–98%.

3. The method according to claim 1, wherein the biodegradable porous polymer scaffold has an open cell structure in which pores are interconnected with each other.

4. The method according to claim 1, wherein the biodegradable polymer is at least one selected from the group consisting of polyglycolic acid (PGA), polylactic acid (PLA), lactic acid-glycolic acid copolymer (PGLA), poly-ε-caprolactone (PCL), polyamino acid, polyanhydride, polyorthoester, and copolymers thereof.

5. The method according to claim 1, wherein the molecular weight of the biodegradable polymer is in the range of 5,000 to 2,000,000.

6. The method according to claim 1, wherein the concentration of the biodegradable polymer in the polymer solution is 5–15% by weight.

7. The method according to claim 1, wherein a solvent used in the polymer solution is selected from the group consisting of chloroform, dichloromethane, acetone, dioxane, tetrahydrofuran, and mixtures thereof.

8. The method according to claim 1, wherein the carbonate in the effervescent mixture is a substance harmless to the human body, which can be used in a medicine and can be easily dissolved in water, having a size of 10–500 $\mu$m.

9. The method according to claim 1, wherein the carbonate in the effervescent mixture is at least one selected from the group consisting of sodium bicarbonate, sodium carbonate, ammonium bicarbonate, ammonium carbonate, potassium bicarbonate, potassium carbonate, calcium carbonate, and mixtures thereof.

10. The method according to claim 1, wherein the organic acid in the effervescent mixture is at least one selected from the group consisting of citric acid, tartaric acid, succinic acid, maleic acid, fumaric acid, malonic acid, malic acid, gluconic acid, mucic acid, amino acids and mixtures thereof.

11. The method according to claim 1, wherein the weight ratio of the effervescent mixture to the polymer is 5/1–20/1.

12. The method according to claim 1, wherein the molar ratio of the organic acid to the carbonate in the effervescent mixture is in the range from 1:1 to 1:3.

13. The method according to claim 1, wherein the alcohol used in the effervescent medium is selected from the group consisting of ethanol, methanol, isopropyl alcohol, and mixtures thereof.

14. The method according to claim 1, wherein the content of alcohol in the aqueous alcoholic solution is 1–95% by volume.

15. The method according to claim 1, wherein the effervescing (foaming) is accompanied by the use of a physical method selected from the group consisting of ultrasonification, microwaving, and agitation.

16. The method according to claim 1, wherein the drying is performed by freeze-drying or vacuum-drying at room temperature, or vacuum-drying below the glass transition temperature of the biodegradable polymers used.

* * * * *

UNITED STATES PATENT AND TRADEMARK OFFICE
CERTIFICATE OF CORRECTION

| | |
|---|---|
| PATENT NO. | : 6,562,374 B1 |
| APPLICATION NO. | : 09/699213 |
| DATED | : May 13, 2003 |
| INVENTOR(S) | : Dong Han et al. |

It is certified that error appears in the above-identified patent and that said Letters Patent is hereby corrected as shown below:

On the title page item (73), add --Biomedlab Corporation, Seoul (KR)--

Signed and Sealed this

Eighteenth Day of September, 2007

JON W. DUDAS
*Director of the United States Patent and Trademark Office*